US009687830B2

(12) United States Patent
Ouyang et al.

(10) Patent No.: US 9,687,830 B2
(45) Date of Patent: Jun. 27, 2017

(54) HIGHLY ACTIVE, SELECTIVE, ACCESSIBLE, AND ROBUST ZEOLITIC SN-BAEYER-VILLIGER OXIDATION CATALYST

(71) Applicants: The Regents of the University of California, Oakland, CA (US); Chevron U.S.A. Inc., San Ramon, CA (US)

(72) Inventors: Xiaoying Ouyang, El Cerrito, CA (US); Stacey Ian Zones, San Francisco, CA (US); Alexander S. Katz, Richmond, CA (US)

(73) Assignees: Chevron U.S.A., Inc., San Ramon, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/847,845

(22) Filed: Sep. 8, 2015

(65) Prior Publication Data
US 2016/0067692 A1    Mar. 10, 2016

Related U.S. Application Data

(60) Provisional application No. 62/047,469, filed on Sep. 8, 2014.

(51) Int. Cl.
*B01J 29/86* (2006.01)
*C07D 313/10* (2006.01)

(52) U.S. Cl.
CPC ............ *B01J 29/86* (2013.01); *C07D 313/10* (2013.01)

(58) Field of Classification Search
CPC ................. B01J 29/86; C07D 313/10
See application file for complete search history.

(56) References Cited

U.S. PATENT DOCUMENTS

| | | | |
|---|---|---|---|
| 6,468,501 B1 | 10/2002 | Chen et al. | |
| 7,084,305 B2 | 8/2006 | Zones et al. | |
| 9,522,390 B2 | 12/2016 | Katz et al. | |
| 2014/0241982 A1 | 8/2014 | Zones et al. | |
| 2014/0356280 A1 | 12/2014 | Ouyang et al. | |

OTHER PUBLICATIONS

International Search Report from corresponding application PCT/US15/48951, mailed Nov. 26, 2015.
Pei Li et al., "Postsynthesis and selective oxidation properties of nanosized Sn-beta zeolite", J. Phys. Chem. C., 2011, vol. 115 pp. 3663-3670.
Xiaoying Ouyang et al., "Novel surfactant-free route to delaminated all-silica and titanosilicate zeolites derived from a layered borosilicate MWW precursor", Dalton Trans., 2014, vol. 43, pp. 10417-10429.
Michael Renz et al., "Selective and shape-selective Baeyer-Villiger oxidations of aromatic aldehydes and cyclic ketones with Sn-beta zeolites and H2O2", Chem. Eur. J., 2002, vol. 8, pp. 4708-4717.
Helen Y. Luo et al., "Synthesis and catalytic activity of Sn-MFI nanosheets for the Baeyer-Villiger oxidation of cyclic ketones", ACS Catal., 2012, vol. 2, pp. 2695-2699.
Guanqi Liu et al., "Hydrothermal synthesis of MWW-type stannosilicate and its post-structural transformation to MCM-56 analogue", Microporous and Mesoporous Materials, 2013, vol. 165, pp. 210-218.
Xiaoying Ouyang et al., "Single-step delamination of a MWW borosilicate layered zeolite precursor under mild conditions without surfactant and sonication", J. Am Chem. Soc., 2014, vol. 136, pp. 1449-1461.
Lingling Wang, et al., "Post-transformation of MWW-type lamellar precursors into MCM-56 analogues", Microporous and Mesoporous Materials 113 (2008), 435-444.
Yong Wang, et al., "Postsynthesis, Characterization, and Catalytic Properties of Aluminosilicates Analogous to MICM-56", Journal of Physical Chemistry C 2009, 113, 18753-18760.
Guanqi Liu, et al., "Hydrothermal synthesis of MWW-type stannosilicate and its post-structural transformation to MCM-56 analogue", Microporous and Mesoporous Materials 165 (2013), 210-218.
Wieslaw J. Roth, et al., "Postsynthesis Transformation of Three-Dimensional Framework into a Lamellar Zeolite with Modifiable Architecture", Journal of the American Chemical Society 2011, 133, 6130-6133.
Pavla Chlubná, et al., "3D to 2D Routes to Ultrathin and Expanded Zeolitic Materials", Chemistry of Materials 2013, 25, 542-547.
Roberto Millini, et al., "Synthesis and characterization of boron-containing molecular sieves", Topics in Catalysis 9 (1999), 13-34.
R. de Ruiter, et al., "Calcination and deboronation of [B]-MFI single crystals", Zeolites, 1993, vol. 13, February.
S. Laforge, et al., "m-Xylene transformation over H-MCM-22 zeolite. 1. Mechanisms and location of the reactions", J. Catal. 220 (2003), 92-103.
S. Laforge, et al., "m-Xylene transformation over H-MCM-22 zeolite. 2. Method for determining the catalytic role of the three different pore systems", Microporous and Mesoporous Materials 67 (2004), 235-244.
S. Laforge, et al., "m-Xylene transformation over H-MCM-22 zeolite. 3. Role of the three pore systems in 0-, m- and o-xylene transformations", Appl. Catal. A: Gen. 268 (2004), 33-41.
P. Matias, et al., "n-Heptane transformation over a HMCM-22 zeolite: Catalytic role of the pore systems", Appl. Catal. A: Gen. 351 (2008), 174-183.
Justin M. Notestein, et al., "Structural Assessment and Catalytic Consequences of the Oxygen Coordination Environment in Grafted Ti-Calixarenes", Journal of the American Chemical Society 2007, 129, 1122-1131.

(Continued)

Primary Examiner — Samantha Shterengarts
Assistant Examiner — Matt Mauro
(74) Attorney, Agent, or Firm — E. Joseph Gess; Melissa M. Hayworth

(57) ABSTRACT

Provided is a process of conducting a Baeyer-Villiger oxidation which comprises contacting a ketone and an oxidant in the presence of an Sn-DZ-1 catalyst to thereby oxidize the ketone to an ester. The Sn-DZ-1 catalyst comprises Sn heteroatoms on the external surface of the zeolitic material lattice framework, and B heteroatoms, or silanols created from boron hydrolysis, throughout the remainder of the lattice framework.

14 Claims, 5 Drawing Sheets

(56) References Cited

OTHER PUBLICATIONS

P. Matias, et al., "Methylcyclohexane transformation over HMCM22 zeolite: Mechanism and location of the reactions", J. Catal. 259 (2008), 190-202.

International Search Report from corresponding application PCT/US15/048918 mailed Jun. 23, 2016.

Nur, H., et al., "Phase-boundary catalysis of alkene epoxidation with aqueous hydrogen peroxide using amphiphilic zeolite particles loaded with titanium oxide" Journal of Catalysis, 2001, vol. 204, No. 2, pp. 402-408.

Jarupatrakorn, J., et al., "Silica-supported, single-site titanium catalysts for olefin epoxidation. A molecular precursor strategy for control of catalyst structure", Journal of the American Chemical Society, 2002, vol. 124, No. 28, pp. 8380-8388.

van der Waal, J. C., et al., "Zeolite titanium beta: A versatile epoxidation catalyst. Solvent effects", Journal of Molecular Catalysis A: Chemical, 1997, vol. 124, No. 2, pp. 137-146.

Ogino, I. et al., "Heteroatom-Tolerant Delamination of Layered Zeolite Precursor Materials", Chemistry of Materials, 2013, vol. 25, No. 9, pp. 1502-1509.

HIGHLY ACTIVE, SELECTIVE, ACCESSIBLE, AND ROBUST ZEOLITIC SN-BAEYER-VILLIGER OXIDATION CATALYST

RELATED APPLICATIONS

This application claims priority to U.S. Provisional No. 62/047,469, filed Sep. 8, 2014, the contents of which are incorporated herein by reference in their entirety.

BACKGROUND OF THE INVENTION

Field of the Invention

The current invention describes the use of framework-substituted zeolitic catalysts that are synthesized by substituting framework heteroatoms for B on the external surface of a zeolitic material. In a particular embodiment of this invention, the heteroatom is Sn and the Lewis-acid catalyst is a solid Baeyer-Villiger oxidation catalyst that uses hydrogen peroxide as an oxidant. Described are the surprisingly advantageous properties of the resulting catalyst in terms of its accessibility, activity, selectivity, and general robustness with regard to the Baeyer-Villiger reaction, all of which crucially depend on the nature of the zeolitic framework.

Description of the Related Art

Zeolites demonstrate extraordinary catalytic utility due to their well-defined catalytic active sites consisting of heteroatoms substituted within the zeolitic framework as well as shape selectivities. However, zeolites have been limited to microporous frameworks in the past, which has limited reactant substrates to small molecules. Incorporating greater accessibility into zeolite catalysts would be invaluable to expanding the scope of their catalysis to include larger and sterically more bulky substrate and product molecules.

MWW layered zeolite precursors, when substituted with metal heteroatoms, have shown catalytic activity using sterically bulky reactants, such as Ti-catalyzed epoxidation of cyclooctene using tertbutylhydroperoxide as oxidant; Al-catalyzed cracking of 1,3,5-triisopropylbenzene, and Sn-catalyzed Baeyer-Villiger oxidation of 2-adamantanone (Wang, L.; Wang, Y.; Liu, Y.; Chen, L.; Cheng, S.; Gao, G.; He, M.; Wu, P. *Microporous and Mesoporous Materials* 2008, 113, 435; Wang, Y.; Liu, Y.; Wang, L.; Wu, H.; Li, X.; He, M.; Wu, P. *Journal of Physical Chemistry C* 2009, 113, 18753; and Liu, G.; Jiang, J.-G.; Yang, B.; Fang, X.; Xu, H.; Peng, H.; Xu, L.; Liu, Y.; Wu, P. *Microporous and Mesoporous Materials* 2013, 165, 210.) Another promising approach for synthesis of accessible zeolites is the transformation of three-dimensional UTL germanosilicate into a two-dimensional lamellar zeolite by Cejka et al., who demonstrated that layers are separated during hydrolysis of the double-four ring (D4R) bridging units by hydrolysis (Roth, W. J.; Shvets, O. V.; Shamzhy, M.; Chlubna, P.; Kubu, M.; Nachtigall, P.; Cejka, J. *Journal of the American Chemical Society* 2011, 133, 6130; and Chlubna, P.; Roth, W. J.; Greer, H. F.; Zhou, W.; Shvets, O.; Zukal, A.; Cejka, J.; Morris, R. E. *Chemistry of Materials* 2013, 25, 542.) This latter approach, while elegant, requires precursors to consist of D4R units in the space between layers, such that D4R removal via hydrolysis results in two-dimensional zeolite layers, and has only been synthetically demonstrated on zeolite UTL.

Borosilicate zeolites have historically been generally considered to be less useful for acid-catalyzed reactions because their intrinsically weak acidity can effectively catalyze reactions that require mild acidity (Millini, R.; Perego, G.; Bellussi, G. *Topics in Catalysis* 1999, 9, 13; Chen, C. Y., Zones, S. I., Hwang, S. J., Bull, L. M. In *Recent Advances in the Science and Technology of Zeolites and Related Materials*, Pts a-C; VanSteen, E., Claeys, M., Callanan, L. H., Eds. 2004; Vol. 154, p 1547; and Chen, C. Y., Zones, S. I. In *13th International Zeolite Conference*; Galarneau, A., Di Renzo, F., Fujula, F., Vedrine, J., Eds.; Elsevier: Amsterdam, 2001, p paper 26.) However, borosilicate zeolites provide a unique route for synthesizing many types of isomorphous forms of zeolites at certain Si/M ratios (M=Al, Ga, Ti, etc.), which offer opportunities for synthesizing heteroatom-substituted metallosilicate zeolites, where the metal ions might otherwise be difficult to incorporate into the framework during direct synthesis (Chen, C. Y.; Zones, S. I. In *13th International Zeolite Conference*; Galarneau, A., Di Renzo, F., Fujula, F., Vedrine, J., Eds.; Elsevier: Amsterdam, 2001, p paper 11.) In such a modification of one framework metal for another, the B atoms template certain T-positions in the zeolitic framework, and silanol nests can be created upon deboronation (Deruiter, R.; Kentgens, A. P. M.; Grootendorst, J.; Jansen, J. C.; Vanbekkum, H. *Zeolites* 1993, 13, 128; and Hwang, S. J.; Chen, C. Y.; Zones, S. I. *Journal of Physical Chemistry B* 2004, 108, 18535.)

Aluminum (Al) heteroatoms have been exchanged or substituted for boron (B) heteroatom in zeolites for many years. This exchange changes a weak acid zeolite into one that is more highly acid. Catalysis by acid sites can impact rates of chemical reaction, rates of mass transfer, selectivity to products and deactivation of the catalytic site or pore system. Better control of the acid sites would help to provide selective control of the overall catalysis.

Though substitution of aluminum for boron has previously been used, the result has been the extremes: the use of 10-MR zeolites where essentially no heteroatom exchange occurs (e.g., ZSM-11) or the use of large- or extra-large pore zeolites where essentially all B heteroatoms are exchanged (e.g., SSZ-33). See, for example, Chen, C. Y.; Zones, S. I., "Method for Heteroatom Lattice Substitution in Large and Extra-Large Pore Borosilicate Zeolites," U.S. Pat. No. 6,468,501 B1, Oct. 22, 2002; Chen, C. Y.; Zones, S. I., "Method to Improve Heteroatom Lattice Substitution in Large and Extra-Large Pore Borosilicate Zeolites," U.S. Pat. No. 6,468,501 B1, Sep. 14, 2004; Chen, C. Y.; Zones, S. I. In *Studies in Surface Science and Catalysis*"; Galarneau, A., Fajula, F., Di Renzo, F., Vedrine, J., Eds.; Elsevier: 2001; Vol. 135; Chen, C. Y.; Zones, S. I. In *Zeolites and Catalysis*; and Čejka, J., Corma, A., Zones, S. I., Eds. 2010, Vol. 1, p. 155. In these instances, acidic conditions are preferred to prevent dissolution of Si from the framework. In the aqueous Al(NO$_3$)$_3$ solution used, the hydrated aluminum cations used in the Al-exchange are too large to enter the 10-MR pores such as ZSM-11. See, for example, Chen, C. Y.; Zones, S. I. In *Studies in Surface Science and Catalysis*, Galarneau, A., Fajula, F., Di Renzo, F., Vedrine, J., Eds., Elsevier: 2001, Vol. 135; Chen, C. Y.; Zones, S. I. In *Zeolites and Catalysis*, Čejka, J., Corma, A., Zones, S. I., Eds. 2010, Vol. 1, p. 155. In the Al-exchange of B-SSZ-33, the Si/B values increase from 18 to more than 200, and Si/Al values from 12 to 24, indicating exchange of most B heteroatoms for Al. See, Chen, C. Y.; Zones, S. I. In *Studies in Surface Science and Catalysis*, Galarneau, A., Fajula, F., Di Renzo, F., Vedrine, J., Eds., Elsevier: 2001, Vol. 135. The result is that either all or none of the boron was exchanged. No selective control is possible.

Catalysis by MCM-22, an aluminosilicate containing Al heteroatoms throughout the lattice framework, and therefore in all three pore systems, is characterized as between a largeand a medium-pore zeolite because it consists of both 10-MR (medium) and 12-MR (large) pores. The role of the acid sites on the external surface hemicages has been determined to differ from those of the internal pore systems through experiments that poison or coke (i.e., formation of carbonaceous deposits in the pore system) the catalytic sites. See, Laforge, S.; Martin, D.; Paillaud, J. L.; Guisnet, M. *J. Catal.* 2003, 220, 92; Laforge, S.; Martin, D.; Guisnet, M. *Microporous Mesoporous Mater.* 2004, 67, 235; Laforge, S.; Martin, D.; Guisnet, M. *Appl. Catal. A: Gen.* 2004, 268, 33; Matias, P.; Lopes, J. M.; Laforge, S.; Magnoux, P.; Guisnet, M.; Ramôa Ribeiro, F. *Appl. Catal. A: Gen.* 2008, 351, 174; Matias, P.; Lopes, J. M.; Laforge, S.; Magnoux, P.; Russo, P. A.; Ribeiro Carrott, M. M. L.; Guisnet, M.; Ramôa Ribeiro, F. *J. Catal.* 2008, 259, 190.

To selectively be able to use acid sites on the external surface would greatly improve one's ability to control a catalysis, and would be of great value to the industry. Moreover, to be able to further enhance a particular reaction by selecting the correct framework of the catalyst would yield even greater benefits to the industry.

SUMMARY OF THE INVENTION

Provided is a process of conducting a Baeyer-Villiger oxidation which comprises contacting a ketone and an oxidant in the presence of a Sn-DZ-1 catalyst to thereby oxidize the ketone to an ester. In one embodiment the ketone comprises a reactive ketone. In a preferred embodiment the reactive ketone is a cyclic ketone, such as adamantanone, and the product is a cyclic ester—a lactone. In one embodiment, the Sn-DZ-1 catalyst is prepared by delaminating a borosilicate zeolite precursor, which delamination is achieved by contacting the zeolite precursor in a solution with a metal salt. In one embodiment, the borosilicate zeolite precursor is ERB-1. Generally, the Sn-substituted delaminated ERB-1 catalyst comprises Sn heteroatoms on the external surface of the zeolite material lattice framework, and B heteroatoms, or silanols created from boron hydrolysis, throughout the remainder of the lattice framework.

Among other factors, it has been found that by using framework-substituted zeolitic catalysts that are synthesized by substituting framework heteroatoms for boron on the external surface of a zeolite material, and in particular where the heteroatom is Sn, surprising advantages are realized for a Bayer-Villiger oxidation reaction. These advantages relate to the accessibility, activity, selectivity and general robustness of the catalyst in the Baeyer-Villiger reaction. All of the advantages have been found to depend on the nature of the zeolite framework, including the Sn heteroatom on the external surface of the zeolite material.

DETAILED DESCRIPTION OF THE PREFERRED EMBODIMENTS

Figure 1:
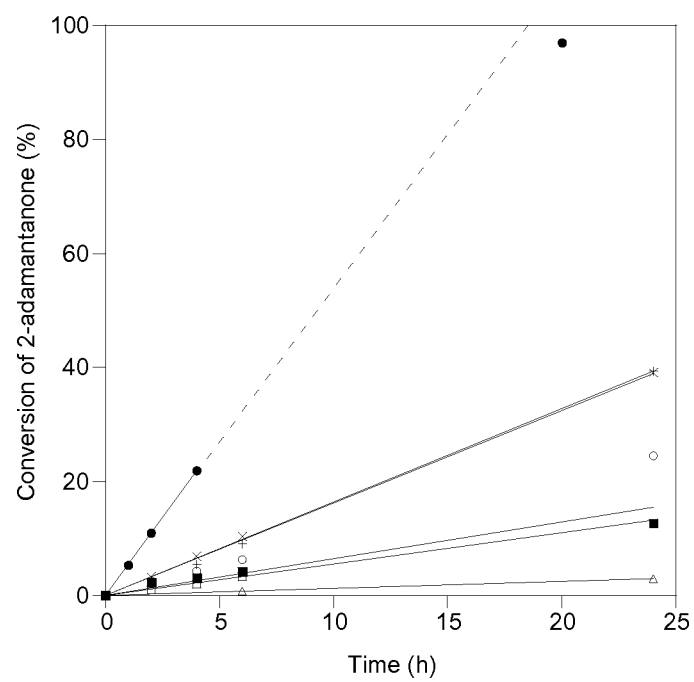
FIG. 1. Catalysis kinetics of 2-adamantanone reacting with $H_2O_2$ over DZ-1 related materials: DZ-1 (Δ), Sn-DZ-1 (Si/Sn=65) (●), Ti-DZ-1 (Si/Ti=67) (○), Zr-DZ-1 (Si/Zr=57) (■), Hf-DZ-1 (Si/Hf=62) (□), Nb-DZ-1 (Si/Nb=40) (x), and Ta-DZ-1 (Si/Ta=39) (+). (Reaction condition: 30 wt % $H_2O_2$ in $H_2O$; $H_2O_2$/2-adamantanone=1.5:1 by mol; 1,4-dioxane as solvent; 75° C.; the molar ratio of Sn to ketone equals 0.0066:1)

Provided is a process of conducting a Baeyer-Villiger oxidation using a selected zeolitic framework catalyst. The catalyst is prepared by a method employing a multistep framework substitution of B heteroatoms of a zeolite, with another heteroatom, in this case Sn, on the external-zeolite surface. This multistep procedure involves first deboronating the zeolite to expose a silanol nest in the framework position previously occupied by B, followed by reaction of the silanol nest with a heteroatom precursor molecule, so as to condense the precursor into the framework, which is substantially similar to the framework position previously occupied by B. In this way, the material comprising the silanol nest is an intermediate between the initial material and final heteroatom-containing catalytic material used in this invention. This general procedure is described in U.S. patent application Ser. No. 14/185,115, "Novel Zeolitic Materials With Heteroatom Substitutions On External Surface Of Lattice Framework", filed Feb. 20, 2014, which application and its disclosure is expressly incorporated herein by reference in its entirety. In an alternate embodiment, substitution of Lewis-acid catalytic heteroatoms into framework positions on the external surface can be accomplished within the context of a delaminated zeolitic material. Examples of such materials are provided in U.S. patent application Ser. No. 13/161,091, "Novel Oxide Material And Synthesis By Fluoride/Chloride Anion Promoted Exfoleation", filed Jun. 15, 2011, which application is expressly incorporated herein by reference in its entirety; and, U.S. patent application Ser. No. 14/291,489, "Delamination Of Borosilieate Layered Zeolite Precursors," filed May 30, 2014, which application is expressly incorporated by reference herein in its entirety.

The advantage of delaminated materials is their generally greater external surface area (on a per gram basis) relative to the three-dimensional (undelaminated) zeolite counterparts. This leads to higher heteroatom loadings upon substitution and, ultimately, higher catalytic activity due to the higher accessible heteroatom-active-site number density, relative to what is available in the three-dimensional (undelaminated) zeolite counterpart.

In one embodiment of the present invention, the Sn site is made more catalytically active, selective, and robust by virtue of it being a Sn heteroatom that is located within the zeolitic framework. A crucial feature of the zeolitic environment is to enforce a particular geometry surrounding the Sn atom in terms of bond angles and distances between framework oxygens. This geometry is conducive to rendering the Sn site more catalytically active, selective, and robust in a manner that depends on the identity, connectivity, and structure of the zeolite framework. In a particularly preferred embodiment of the present invention, the resulting catalyst is active for the Baeyer-Villiger oxidation of 2-adamantanone using hydrogen peroxide as the oxidant, for which Sn-substituted DZ-1 catalyst (denoted as Sn-DZ-1) has been found to be the most active metal heteroatom-substituted DZ-1 material. Furthermore, comparison of Sn-DZ-1 with Sn-Beta for Baeyer-Villiger oxidation using ketones substrates of various steric bulkiness shows that the delaminated zeolite Sn-DZ-1 is far more active for bulkier ketone substrates (e.g., 5-bromo-2-adamantanone and 5-hydroxyl-2-adamantanone), both on a per catalyst weight as well as a per Sn-cite basis, probably due to its higher accessibility of Sn sites.

The role of the framework is demonstrated by comparing Sn-cite basis, as well as per delaminated zeolite Sn-DZ-1 with Sn-UCB-4. The former (Sn-DZ-1) exhibits a significantly higher activity for Baeyer Villiger oxidation. Yet when comparing Ti-DZ-1 with Ti-UCB-4, it is the latter that exhibits a significantly higher activity for olefin epoxidation with organic hydroperoxide. Therefore, the choice of the zeolite framework is highly nonobvious and can be both dependent on the reaction (olefin epoxidation versus Baeyer-Villiger oxidation) and metal heteroatom (i.e. Sn versus Ti) composition. In a most preferred aspect of the present invention, the catalyst for Baeyer-Villiger oxidation is Sn-DZ-1, which, by virtue of its Sn sites being on the external surface, is most preferred for bulky reactant substrates (substrates that have a lower catalytic activity when used with Sn-Beta zeolite due to lack of ability to penetrate microporous channels of Sn-Beta where Sn sites are located). Sn-DZ-1 catalyst is synthesized by (i) delaminating boron-containing ERB-1 and synthesizing silanol nests in locations previously occupied by boron—with synthesis of material DZ-1, followed by (ii) reoccupying some of these silanol nests located on the external surface of the delaminated zeolite with grafted Sn heteroatoms via condensation of a Sn precursor to the silanol nests, as discussed in U.S. patent application Ser. No. 14/291,489, "Delamination of Borosilieate Layered Zeolite Precursors," filed May 30, 2014, which application is expressly incorporated by reference herein in its entirety.

The process of the present invention, therefore, is a process of conducting a Baeyer-Villiger oxidation which comprises contacting a ketone and an oxidant in the presence of an Sn-DZ-1 catalyst. The ketone is oxidized to an ester. The ketone can be any reactive ketone. In a preferred embodiment the reactive ketone is a cyclic ketone and the Baeyer-Villiger-oxidation product is a cyclic ester—a lactone. The ketone can be, for example, 2-adamantanone, 5-hydroxyl-2-adamantanone or 5-bromo-2-adamantanone. The oxidant can be any suitable oxidant, such as a peroxy acid. In one embodiment, the oxidant comprises hydrogen peroxide. In using a solvent for the reaction, a solvent such as dioxane is suitable.

The Sn-DZ-1 catalyst is generally prepared by delaminating a borosiliate zeolite precursor. This is achieved by contacting the zeolite precursor in a solution with a metal salt, e.g., as described in U.S. patent application Ser. No. 14/291,489, noted above.

In another embodiment, the process of the present invention involves conducting a Baeyer-Villiger oxidation which comprises contacting a ketone and an oxidant in the presence of a Sn-substituted delaminated ERB-1 catalyst. The Sn-substituted, delaminated ERB-1 catalyst comprises Sn heteroatoms on the external surface of the zeolite material lattice framework, and B heteroatoms, or silanols created from boron hydrolysis, throughout the remainder of the lattice framework.

The following examples are provided to further illustrate the present invention, but are not meant to be limiting.

Details of Synthesis and Characterization of Materials Prepared for Use in the Examples Synthesis of ERB-1 Precursor (ERB-1P).

The synthesis of this material followed known and previously described procedures. In the procedure, 2.40 g of NaOH (EMD Chemicals, 97%) and 6.18 g of $H_3BO_3$ (≥99.5%, Fisher Chemical) were dissolved in 30 mL of nanopure $H_2O$, and 12.8 g of PI (≥99.5%, purified by redistillation, Sigma-Aldrich). To this mixture, 9.0 g of $SiO_2$ (Aerosil® 200, Evonik-Degussa) and 0.10 g of seed crystals (as-made ERB-1P, Si/B=11) were added. A white viscous gel was obtained after mixing with a spatula. The gel composition in molar ratios was $SiO_2$:0.33 $B_2O_3$:0.2 $Na_2O$: 1.0 PI:11.0 $H_2O$. This gel was subsequently transferred to a 125 mL Parr reactor equipped with a Teflon liner. The reactor was heated at 175° C. for a period of 7-9 days without agitation. After cooling, the contents were poured into a filter, and the precipitated solids were washed several times with deionized water and then air dried. The characterization of material ERB-1 after calcination (denoted ERB-1C) matches previous specifications for this material.

Synthesis of DZ-1.

The synthesis of this material followed known and previously described procedures. In this procedure, 1.0 g of zeolite precursor and either 4.0 g of $Zn(NO_3)_2.6H_2O$ or $Mn(NO_3)_2.4H_2O$ were added to 35 g of pH 1 $HNO_3$ solution in a 125 mL sealed thick-walled glass reactor, under vigorous stirring. The mixture was heated at 135° C. for 16 h. The resulting delaminated material was denoted as DZ-1. The solid product was collected on a filter, washed thoroughly with water, and finally air-dried. The characterization of material DZ-1 matches previous specifications for this material.

Synthesis of Ti-DZ-1.

The synthesis of this material was described previously and is also described herein for completion. In this procedure, 4 g $Ti(OC_4H_9)_4$ was added to 1 g of DZ-1 to make a viscous slurry in a sealed, thick-walled glass reactor at 150° C. The slurry was vigorously stirred for 1 h. Then the temperature of 120° C. was lowered and 20 mL of n-BuOH was added into the slurry. The resulting slurry was stirred for an additional 10 min. The solid product was collected on a filter, washed thoroughly with n-BuOH to remove residual $Ti(OC_4H_9)_4$ and surface-grafted Ti species, followed by acetone to remove residual n-BuOH, and finally was air-dried. The resulting material is denoted as Ti-DZ-1, and its full characterization is consistent with that previously described. The characterization of material Ti-DZ-1 matches previous specifications for this material.

Synthesis of B-SSZ-70 Precursor.

B-SSZ-70 precursor was synthesized using the same method as described in I. Ogino, E. A. Eilertsen, S.-J. Hwang, T. Rea, D. Xie, X. Ouyang, S. I. Zones, A. Katz, *Chem. Mater.*, 2013, 25, 1502-1509. Gel compositions were $SiO_2$: 0.033 $B_2O_3$: 0.050 $Na_2O$: 0.20 SDA (1,3-bis(isobutyl) imidazolium): 30 $H_2O$. The gel was sealed in a 23-mL Parr reactor and heated while tumbling the reactor at 60 rpm at 150° C. for a period of 1-2 weeks. After cooling, the contents were poured into a filter, and the precipitated solids were washed several times with water and then air dried.

Synthesis of UCB-4.

UCB-4 was synthesized based on previous literature. In this procedure, a mixture of 0.50 g of B-SSZ-70 precursor, 0.55 g of cetyltrimethylammonium bromide (CTAB), 0.85 g of tetrabutylammonium fluoride trihydrate (TBAF), and 0.85 g of tetrabutylammonium chloride (TBACl) in 20 mL of DMF was placed in a sealed, thick-walled glass reactor, and stirred at 100° C. for 72 h in an oil bath. After cooling, the slurry was sonicated for 1 h in an ice bath, using a Branson digital sonifier 450 (Branson, USA) operating under pulse mode (1.0 s on and 0.1 s off). The sonicated slurry was filtered, to separate a solid from a brown-colored filtrate. The solid was washed with DMF and then with ethanol, thoroughly, and dried at 60° C. overnight, yielding a white solid, followed by calcination in air at 550° C. (ramp rate 1° C./min from r.t.) for 5 h. The characterization of material UCB-4 matches previous specifications for this material.

Synthesis of Deboronated UCB-4.

20 mL of 2.0 N $HNO_3$ solution was added to 0.50 g of the as-made UCB-4 in a sealed, thick-walled glass reactor, and stirred at 100° C. for 24 h. The solid product was collected on a filter, washed thoroughly with deionized water, and was then air-dried.

Synthesis of Ti-UCB-4.

4 g $Ti(OC_4H_9)_4$ was added to 1 g of deboronated UCB-4 to make a viscous slurry in a sealed, thick-walled glass reactor at 150° C. The slurry was vigorously stirred for 1 h. The temperature was subsequently lowered to 120° C., and 20 mL of n-BuOH was added into the slurry. The resulting slurry was stirred for 10 min. The solid product was collected on a filter, washed thoroughly with n-BuOH to remove residual $Ti(OC_4H_9)_4$ and surface-grafted Ti species, followed by acetone to remove residual n-BuOH, and was finally air-dried. The resulting material is denoted as Ti-UCB-4. The characterization of material Ti-UCB-4 is given in Table 1 and matches previous specifications for this material.

Acid Treatment of Ti-UCB-4.

50 mL of 2 N $HNO_3$ was added to 100 mg of Ti-UCB-4 in a sealed, thick-walled glass reactor at 100° C. The mixture was vigorously stirred for 1 h before being cooled down to room temperature. The solid was collected on a filter, washed thoroughly with deionized water followed by acetone, and was finally air-dried.

While the examples above substitute Ti into the silanol nest created by removing framework boron, it should be mentioned that the substitution of other metals of catalytic relevance and specifically Lewis-acid-catalytic relevance can be achieved using the procedures for the substitution of other metals such as Hf, Nb, Ta, Al, Sn, and Zr instead of Ti, described, for example, in U.S. patent application Ser. No. 14/291,489, noted above.

Synthesis of Sn-DZ-1.

4 g $SnCl_4.5H_2O$ were added to 1 g of DZ-1 in a sealed, thick-walled glass reactor at room temperature in a glove box. A viscous slurry formed after heating this solid mixture to 125° C. under vigorous stirring with a magnetic stir bar. After 1 h (the Sn content within the final material could be adjusted by varying the reaction time at this step between 5 min and 3 h), 20 mL of n-BuOH were added into the slurry, and stirring continued for an additional 10 min. The solid product was collected on a filter, washed thoroughly with n-BuOH followed by acetone to remove residual $SnCl_4$ and weakly anchored Sn species, and finally air-dried. The resulting material was denoted as Sn-DZ-1.

Syntheses of Zr-DZ-1, Hf-DZ-1, Nb-DZ-1.

For synthesis of Zr-DZ-1, 4 g $Zr(OC_4H_9)_4$ was added to 1 g of DZ-1, and the resulting viscous slurry was heated in a sealed, thick-walled glass reactor at 150° C. and vigorously stirred with a stir bar for 1 h. The temperature was lowered to 120° C., and 20 mL of n-BuOH were added to the slurry, after which stirring continued for 10 min. The solid product was collected on a filter, washed thoroughly with n-BuOH followed by acetone to remove residual $Zr(OC_4H_9)_4$ and surface-grafted Zr species, and finally air-dried. The resulting material was denoted as Zr-DZ-1. Similar procedures were followed for synthesis of Hf-DZ-1 and Nb-DZ-1, except that $Hf(OC_4H_9)_4$ and $Nb(OC_2H_5)_4$, respectively, was used instead of $Zr(OC_4H_9)_4$.

TABLE 1

Synthesis Conditions and Physicochemical Properties of DZ-1 Related Materials

| Sample[a] | Hetero-atom (M) | Metal pre-cursor | Si/Ti ratio | Si/B ratio | $V_{micro}$[c] $(cm^3/g)$ | $V_{meso}$[d] $(cm^3/g)$ | $S_{ext}$[e] $(m^2/g)$ |
|---|---|---|---|---|---|---|---|
| ERB-1C | B | n/a | n/a | 10 | 0.12 | 0.04 | 53 |
| UCB-4 | B | n/a | n/a | 30 | 0.12 | 0.08 | 96 |
| DZ-1 | n/a | n/a | n/a[b] | >200 | 0.08 | 0.10 | 131 |

[a]All the samples in Table 1 are calcined materials;
[b]The Si/Zn ratio for DZ-1 is >200;
[c]Micropore volume determined by t-plot method;
[d]Mesopore (between 1 and 10 nm in diameter) volume determined by NLDFT method;
[e]External surface area determined by t-plot method.

Example 1

Baeyer-Villiger (BV) Oxidation Procedure.

The BV reactions were performed on the DZ-1-based materials using the following reaction conditions: catalyst, 0.66 mol % of metal with respect to ketone; ketone, 1 mmol; $H_2O_2$, 1.5 mmol; dioxane, 3 mL; temperature, 75° C. Dodecane was used as an internal standard. The reactions were performed in a 15 ml sealed, thick-walled glass reactor with vigorous stirring. Aliquots from the reaction mixture were sampled and analyzed by gas chromatography (FID detector) using an Agilent 6890 and a 30-m HP-1 column. The lactone products were identified by comparing their retention times. The conversion was calculated based on the total initial amount of ketone.

The accessibility and catalytic activity of heteroatoms substituted in delaminated Lewis-acid zeolites were confirmed using the Baeyer-Villiger oxidation of 2-adamantanone with aqueous hydrogen peroxide at 75° C. as a probe reaction, the chemical equation of which is shown in Scheme 1a.

Scheme 1. Chemical Equations of Baeyer-Villiger oxidation of 2-adamantanone derivatives with $H_2O_2$.

(a)

-continued

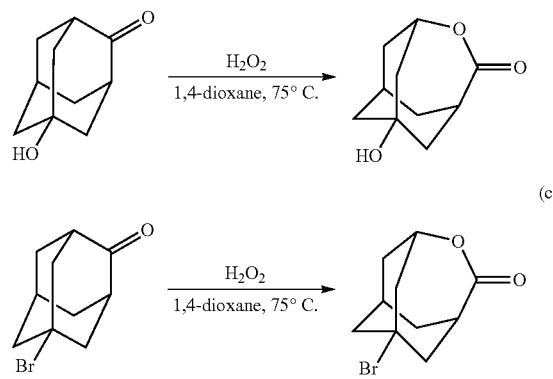

Figure 2:
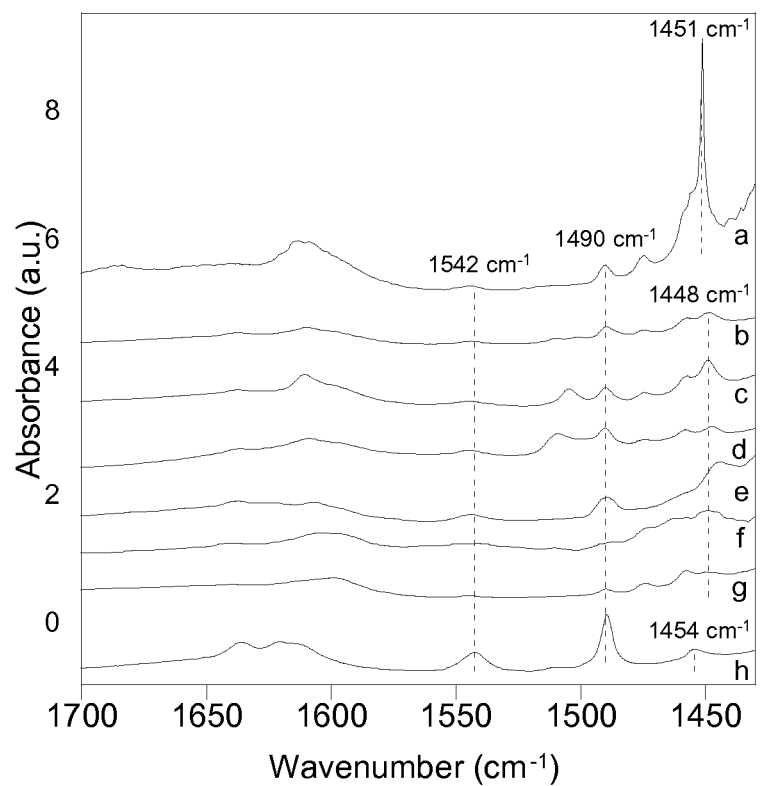
FIG. 2. FTIR spectra of activated samples, (a) Sn-DZ-1, (b) Nb-DZ-1, (c) Ta-DZ-1, (d) Hf-DZ-1, (e) Ti-DZ-1, (f) Zr-DZ-1, (g) DZ-1, and (h) ERB-1-del-135, recorded after pyridine adsorption at 25° C. and desorption at 150° C.

The catalytic performance of DZ-1-based delaminated zeolites consisting of different metal heteroatoms, and kinetics data are shown in FIG. 1 and are summarized Table 2 below. The kinetic data in FIG. 1 show a linear relationship between the conversion of 2-adamantanone and time, suggesting a zero order dependence on 2-adamantanone. Metal-free catalyst consisting of all-silica DZ-1 shows negligible activity for the oxidation of 2-adamantanone. Sn-DZ-1 shows significantly higher activity than other heteroatom-substituted DZ-1 materials comprising either Ti, Zr, Hf, Nb, or Ta heteroatoms, although all DZ-1-based catalysts have nearly 100% product selectivity. The higher activity for the Sn sites compared with other metal heteroatom sites is consistent with the stronger pyridine adsorption exhibited by the Sn sites, as shown by its strongest intensity of the Lewis-acid band (1451 cm$^{-1}$), in FIG. 2(a). Thus these results correlate pyridine adsorption as a measure of Lewis acidity and Baeyer-Villiger catalytic activity.

TABLE 2

BV Oxidation of 2-adamantanone Derivatives with $H_2O_2$ Catalyzed by Sn-DZ-1 and Sn-Beta. [a]

| | Sn-DZ-1 [b] | | Sn-Beta [c] | |
|---|---|---|---|---|
| | Initial rates [d] | | Initial rates [d] | |
| Substrates | [mol h$^{-1}$ (mol Sn)$^{-1}$] | C [e] (%) | [mol h$^{-1}$ (mol Sn)$^{-1}$] | C [e] (%) |
| 2-adamantanone | 866 | 97 | 1963 | 99 |
| 5-hydroxyl-2-adamantanone | 825 | 95 | 417 | 66 |
| 5-bromo-2-adamantanone | 688 | 94 | 366 | 57 |

[a] Reaction condition: 30 wt % $H_2O_2$ in $H_2O$; $H_2O_2$/ketone = 1.5:1 by mol; 1,4-dioxane as solvent; 75° C.; The molar ratio of Sn to ketone equals 0.0066:1);
[b] Si/Sn = 65;
[c] Si/Sn = 100;
[d] Initial rates are calculated by dividing the moles of substrates converted per hour when conversion of substrate is under 20% by moles of Sn sites;
[e] Conversion = (moles of ketone converted at 24 h)/(initial moles of ketone) × 100;
[f] Selectivity = (moles of product at 24 h)/(moles of ketone reacted) × 100. Selectivities for all these catalysts are nearly 100%.

Example 2

In order to investigate the reactivity and accessibility of Sn sites that are located in two vastly differing zeolitic environments (i.e. microporous versus delaminated), the catalytic activity of Sn-DZ-1 (Si/Sn=65) and Sn-Beta (Si/Sn=100) for Baeyer Villiger oxidation was compared using ketones of varying steric bulkiness, as shown in Scheme 1. Sn-Beta has been previously reported to be an active and selective catalyst for Baeyer-Villiger oxidation, where the isolated Sn sites are located within the 3D 12-MR pores and BEA channel system. This is entirely in contrast to Sn-DZ-1, where the Sn sites are located within 12-MR pockets that are near the external surface. Therefore, the accessibility of Sn-Beta for bulky substrates may be expected to be more limited in Sn-BEA than in Sn-DZ-1.

Figure 3A:
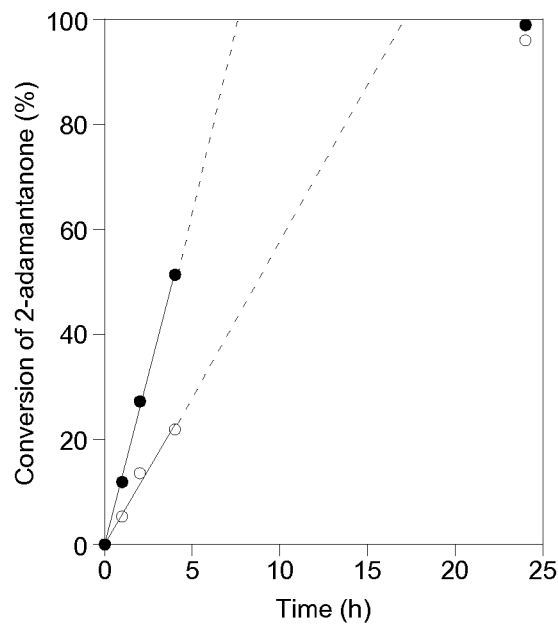
FIG. 3A shows catalysis kinetics of (a) 2-adamantanone.
Figure 3B:
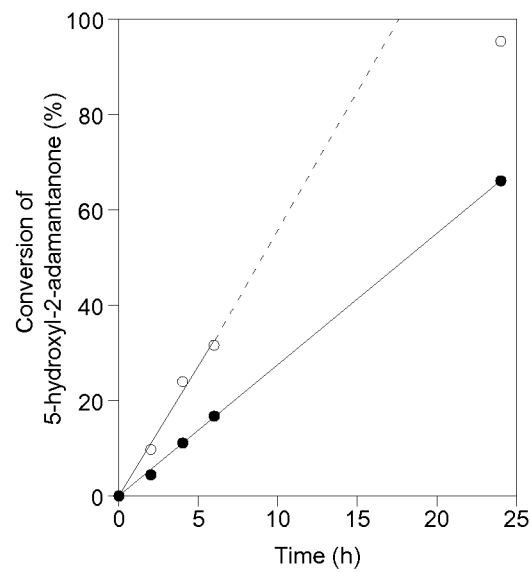
FIG. 3B shows catalysis kinetics of 5-hydroxyl-2-adamantanone.
Figure 3C:
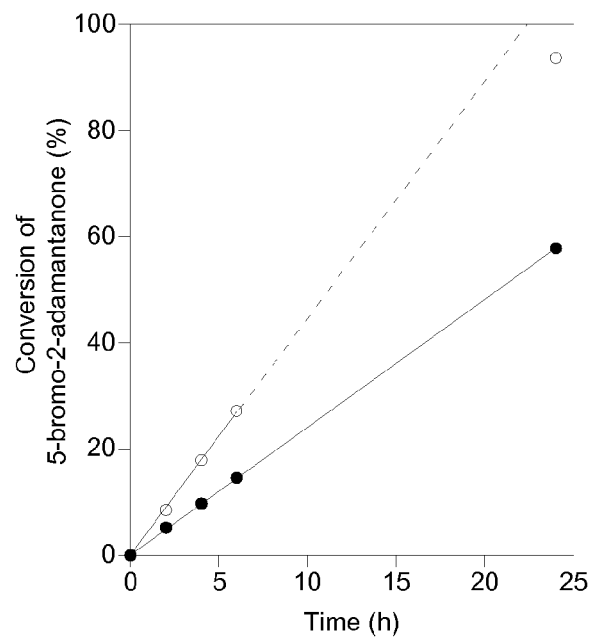
FIG. 3C shows catalysis kinetics of 5-bromo-2-adamantanone reacting with $H_2O_2$ over Sn-DZ-1 (Si/Sn=65) (○) and Sn-Beta (Si/Sn=100) (●). Reaction condition: 30 wt % $H_2O_2$ in $H_2O$; $H_2O_2$/ketone=1.5:1 by mol; 1,4-dioxane as solvent; 75° C.; The molar ratio of Sn to ketone equals 0.0066:1

Baeyer-Villiger kinetics data in FIG. 3A and Table 2 show that when 2-adamantanone is used as the ketone substrate, Sn-Beta shows significantly higher activity than Sn-DZ-1 (1963 mol h$^{-1}$ (mol Sn)$^{-1}$ for Sn-Beta vs 866 mol h$^{-1}$ (mol Sn)$^{-1}$ for Sn-DZ-1). However, FIG. 3B shows that when using the sterically more demanding 5-hydroxyl-2-adamantanone as the ketone substrate, Sn-DZ-1 shows significantly higher activity than Sn-Beta (825 mol h$^{-1}$ (mol Sn)$^{-1}$ for Sn-DZ-1 vs 417 mol h$^{-1}$ (mol Sn)$^{-1}$ for Sn-Beta), which suggests that the activity for Sn-Beta is more limited by the more restricted accessibility than for the delaminated Sn-DZ-1, where all Sn sites are located near the external surface. Similarly, as shown in FIG. 3C, when 5-bromo-2-adamantanone is used as the ketone substrate, Sn-DZ-1 exhibit significantly higher activity than Sn-Beta (688 mol h$^{-1}$ (mol Sn)$^{-1}$ for Sn-DZ-1 vs 366 mol h$^{-1}$ (mol Sn)$^{-1}$ for Sn-Beta). As summarized in Table 2, when the size of the ketone substrate increases from 2-adamantanone to 5-bromo-2-adamantanone, the catalytic activity of Sn-DZ-1 for Baeyer-Villiger oxidation has only decreased by 20%, but the same activity for Sn-Beta catalyst has decreased by 81%. Therefore, it is evident that the Sn sites in Sn-DZ-1 prepared according to our heteroatom-substitution method yields higher accessibility than Sn sites located in internal micropores of three-dimensional zeolites.

Example 3

Figure 4:
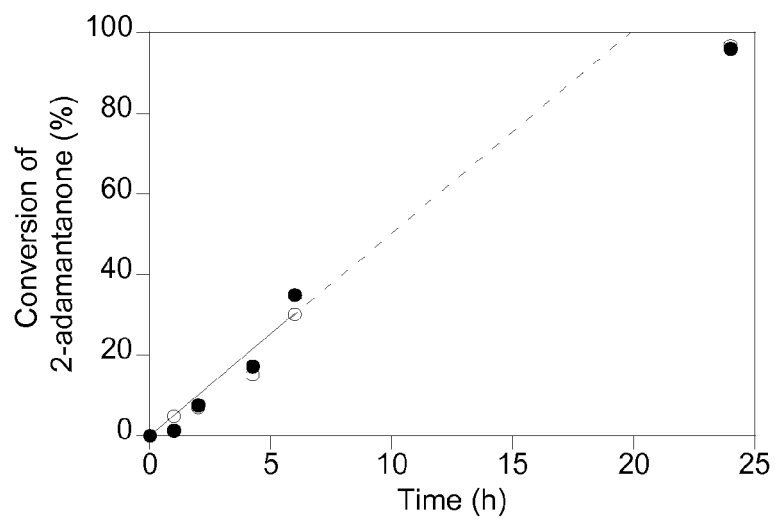
FIG. 4. Catalysis kinetics of 2-adamantanone reacting with $H_2O_2$ over Sn-DZ-1 materials which have Si/Sn ratios of 65 (○) and 94 (●). (Reaction condition: 30 wt % $H_2O_2$ in $H_2O$; $H_2O_2$/2-adamantanone=1.5:1 by mol; 1,4-dioxane as solvent; 75° C.; The molar ratio of Sn to ketone equals 0.0066:1)

To investigate the relationship between the catalytic activity for Baeyer-Villiger oxidation and the proximity of the Sn sites, two batches of Sn-DZ-1 with different Sn contents were prepared, which was accomplished by varying the synthesis time. These two Sn-DZ-1 samples have Si/Sn ratios of 65 and 94. If the reaction requires two Sn sites to work cooperatively, one should expect that the one with lower Si/Sn ratios should have disproportionally higher catalytic activity than the one with higher Si/Sn ratios. The catalytic results shown in FIG. 4 and summarized in Table 3 below suggest that the per-Sn-site activity for each sample is similar: 866 mol h$^{-1}$ (mol Sn)$^{-1}$ for Sn-DZ-1 with Si/Sn=65 and 767 mol h$^{-1}$ (mol Sn)$^{-1}$ for Sn-DZ-1 with Si/Sn=94. Therefore, these results suggest that activity for Baeyer-Villiger oxidation is independent of the local density of Sn sites and is likely accomplished with an isolated Sn site.

TABLE 3

BV Oxidation of 2-adamantanone with H$_2$O$_2$ Catalyzed by Sn-DZ-1 with different Sn content.[a]

| Substrates | Sn-DZ-1 (Si/Sn = 65) | | Sn-DZ-1 (Si/Sn = 94) | |
|---|---|---|---|---|
| | Initial rates[b] [mol h$^{-1}$ (mol Sn)$^{-1}$] | C[c] (%) | Initial rates[b] [mol h$^{-1}$ (mol Sn)$^{-1}$] | C[c] (%) |
| (2-adamantanone structure) | 866 | 97 | 767 | 86 |

Reaction condition: 30 wt % H$_2$O$_2$ in H$_2$O; H$_2$O$_2$/2-adamantanone = 1.5:1 by mol; 1,4-dioxane as solvent; 75° C.; The molar ratio of Sn to ketone equals 0.0066:1);
[b] Initial rates are calculated by dividing the moles of substrates converted per hour when conversion of substrate is under 20% by moles of Sn sites;
[c] Conversion = (moles of ketone converted at 24 h)/(initial moles of ketone) × 100;
[d] Selectivity = (moles of product at 24 h)/(moles of ketone reacted) × 100.

Example 4

Figure 5:
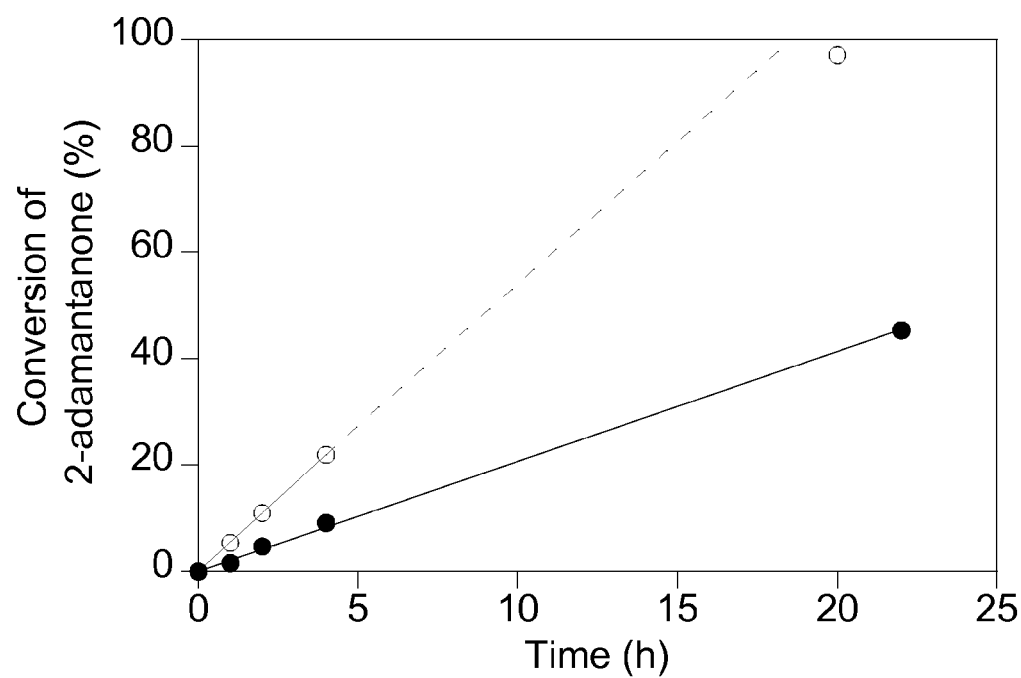
FIG. 5. Catalysis kinetics of 2-adamantanone reacting with $H_2O_2$ over Sn-DZ-1 (Si/Sn=65) (○) and Sn-UCB-4 (Si/Sn=100) (●) materials which have Si/Sn ratios of 65 and 100, respectively. (Reaction condition: 30 wt % $H_2O_2$ in $H_2O$; $H_2O_2$/2-adamantanone=1.5:1 by mol; 1,4-dioxane as solvent; 75° C.; The molar ratio of Sn to ketone equals 0.0066:1)

Two delaminated zeolite environments for Sn sites were compared, consisting of Sn-DZ-1 (Si/Sn=65) and Sn-UCB-4 (Si/Sn=100), for the Baeyer-Villiger oxidation of 2-adamantanone. Relevant kinetics data are shown in FIG. 5 and summarized in Table 4 below, and demonstrate that Sn-DZ-1 is significantly more active than Sn-UCB-4 (866 mol h$^{-1}$ (mol Sn)$^{-1}$ for Sn-DZ-1 vs 355 mol h$^{-1}$ (mol Sn)$^{-1}$ for Sn-Beta), even though they have very similar external surface areas and DR-UV spectra of isolated framework Sn sites. These results suggest that the zeolite framework type has a significant impact on the Sn-site reactivity for Lewis-acid catalyzed reactions, even for half-open sites such as those found near the external surface of delaminated zeolites.

TABLE 4

BV Oxidation of 2-adamantanone with H$_2$O$_2$ Catalyzed by Sn-DZ-1 with different Sn content.[a]

| Substrates | Sn-DZ-1 (Si/Sn = 65) | | Sn-UCB-4 (Si/Sn = 100) | |
|---|---|---|---|---|
| | Initial rates[b] [mol h$^{-1}$ (mol Sn)$^{-1}$] | C[c] (%) | Initial rates[b] [mol h$^{-1}$ (mol Sn)$^{-1}$] | C[c] (%) |
| (2-adamantanone structure) | 866 | 97 | 355 | 45 |

[a] Reaction condition: 30 wt % H$_2$O$_2$ in H$_2$O; H$_2$O$_2$/2-adamantanone = 1.5:1 by mol; 1,4-dioxane as solvent; 75° C.; The molar ratio of Sn to ketone equals 0.0066:1);
[b] Initial rates are calculated by dividing the moles of substrates converted per hour when conversion of substrate is under 20% by moles of Sn sites;
[c] Conversion = (moles of ketone converted at 24 h)/(initial moles of ketone) × 100;
[d] Selectivity = (moles of product at 24 h)/(moles of ketone reacted) × 100.

Baeyer-Village-Catalysis Summary

Heteroatom metal cations consisting of Hf, Nb, Ti, Ta, Sn, and Zr are reinserted into silanol nests within DZ-1, and a subset of these are also reinserted into deboronated UCB-4 as a comparison, all by using reactive metal precursors. Of all heteroatoms investigated, Sn-DZ-1 is the most active DZ-1-based materials for Baeyer-Villiger oxidation. When the small reactant 2-adamantanone is used as the ketone reactant substrate, a reference material Sn-Beta shows higher activity than Sn-DZ-1, but when bulkier ketone substrates (such as 5-hydroxyl-2-adamantanone and 5-bromo-2-adamantanone) are used as ketone substrates, Sn-DZ-1 shows significantly higher activity than Sn-Beta, probably due to the higher accessibility of the Sn sites located in Sn-DZ-1 than in Sn-Beta. When the concentration of framework Sn incorporated in DZ-1 is varied, the activity for Baeyer-Villiger oxidation of 2-adamantanone per site is the same, and this suggests that the Baeyer-Villiger oxidation require the same isolated Sn site, without the need for cooperativity between Sn sites. The role of the framework is first highlighted in catalysis with a comparison of Sn-DZ-1 and Sn-UCB-4 as Baeyer-Villiger oxidation catalysts, where Sn-UCB-4 is much less active than Sn-DZ-1 on a per-Sn-site basis, even though the external surface areas and DR-UV spectra characterizing Sn sites for both materials of the two delaminated zeolite materials are similar.

What is claimed is:

1. A process of conducting a Baeyer-Villiger oxidation which comprises contacting a ketone and an oxidant in the presence of a Sn-DZ-1 catalyst to thereby oxidize the ketone to an ester, wherein the Sn-DZ-1 catalyst is prepared by a method comprising delaminating ERB-1 layered borosilicate zeolite precursor by contacting the ERB-1 with a solution comprising a metal salt.

2. The process of claim 1, wherein the ketone comprises a cyclic ketone such that its Baeyer-Villiger-oxidation product is a lactone.

3. The process of claim 1, wherein the ketone comprises 2-adamantanone.

4. The process of claim 1, wherein the ketone comprises 5-hydroxyl-2-adamantanone.

5. The process of claim 1, wherein the ketone comprises 5-bromo-2-adamantanone.

6. The process of claim 1, wherein the oxidant comprises a peroxy acid.

7. The process of claim 1, wherein the oxidant comprises hydrogen peroxide.

8. The process of claim 1, wherein the oxidant comprises an organic hydroperoxide.

9. The process of claim 1, wherein a solvent is used for the reaction which comprises dioxane.

10. The process of claim 1, wherein the metal salt comprises an Al, Zn, or Mn cation.

11. The process of claim 1, wherein the metal salt comprises a Ga cation.

12. The process of claim 1, wherein the Sn-DZ-1 comprises Sn heteroatoms on the external surface of the zeolitic material lattice framework, and B heteroatoms, or silanols created from boron hydrolysis, throughout the remainder of the lattice framework.

13. The process of claim 12, wherein the lattice framework comprises large pore 12 member ring or larger openings at the external surface of the framework, and 10 member ring or smaller openings beneath the external surface large pore openings.

14. The process of claim 12, wherein the external surface of the framework comprises 12 member ring openings with 10 member ring openings beneath the external surface 12 member ring openings.

\* \* \* \* \*